(12) United States Patent
Golarits et al.

(10) Patent No.: US 11,524,101 B2
(45) Date of Patent: Dec. 13, 2022

(54) BLOOD TREATMENT DEVICE WITH IMPROVED BAG WEIGHT MONITORING

(71) Applicant: B. Braun Avitum AG, Melsungen (DE)

(72) Inventors: István Golarits, Budapest (HU); Botond Tényi, Budapest (HU)

(73) Assignee: B. Braun Avitum AG, Melsungen (DE)

( * ) Notice: Subject to any disclaimer, the term of this patent is extended or adjusted under 35 U.S.C. 154(b) by 271 days.

(21) Appl. No.: 17/030,572

(22) Filed: Sep. 24, 2020

(65) Prior Publication Data

US 2021/0093765 A1  Apr. 1, 2021

(30) Foreign Application Priority Data

Sep. 26, 2019  (DE) ...................... 10 2019 126 047.7

(51) Int. Cl.
*A61M 1/16* (2006.01)
*A61M 1/36* (2006.01)
*A61M 1/26* (2006.01)

(52) U.S. Cl.
CPC .......... *A61M 1/1601* (2014.02); *A61M 1/267* (2014.02); *A61M 1/3621* (2013.01); *A61M 2205/18* (2013.01); *A61M 2205/3393* (2013.01)

(58) Field of Classification Search
CPC .. A61M 1/1601; A61M 1/1643; A61M 1/267; A61M 1/3621; A61M 2205/18; A61M 2205/3393
See application file for complete search history.

(56) References Cited

U.S. PATENT DOCUMENTS

| 5,112,298 A | 5/1992 | Prince et al. |
| 9,999,716 B2 | 6/2018 | Golarits et al. |

(Continued)

FOREIGN PATENT DOCUMENTS

| DE | 102017111803 A1 | 12/2018 |
| EP | 0611228 A2 | 8/1994 |

(Continued)

OTHER PUBLICATIONS

Extended European Search Report received in Application No. 20197633.9-1113 dated Feb. 19, 2021, with translation, 13 pages.

(Continued)

*Primary Examiner* — Dirk R Bass
(74) *Attorney, Agent, or Firm* — Christopher A. Rothe; Culhane Meadows, PLLC (57) ABSTRACT

A blood treatment device includes an extracorporeal blood circuit, dialyzer and dialysis fluid circuit. The blood circuit and dialysis fluid circuit are separated from each other by a membrane in the dialyzer. A weighing device measures and monitors the weight of a bag containing a fluid. A fluid pump pumps fluid out of and into the bag. A control unit interrupts fluid supply by stopping the pump when a weight variation of the bag occurs and temporarily maintains the interruption at least until the malfunction disappears, and automatically restarts the fluid supply if the bag or the weight of the bag stabilizes within a predetermined time and the weight variation does not exceed a predetermined value. The control unit generates an alarm if the bag or weight of the bag does not stabilize within a predetermined time and/or if the weight variation exceeds a predetermined value.

10 Claims, 3 Drawing Sheets

(56) References Cited

U.S. PATENT DOCUMENTS

| | | |
|---|---|---|
| 2011/0160649 A1 | 6/2011 | Pan |
| 2016/0121037 A1 | 5/2016 | Golarits et al. |
| 2020/0179584 A1* | 6/2020 | Wabel .................... G01G 21/22 |

FOREIGN PATENT DOCUMENTS

| | | |
|---|---|---|
| EP | 0829265 A1 | 3/1998 |
| EP | 1175238 A | 1/2002 |
| EP | 3034112 A1 | 6/2016 |
| WO | 8501879 A1 | 5/1985 |
| WO | 2016104720 A1 | 6/2016 |

OTHER PUBLICATIONS

German Search Report received in Application No. 10 2019 126 047.7 dated Sep. 10, 2020, 15 pages.

* cited by examiner

BLOOD TREATMENT DEVICE WITH IMPROVED BAG WEIGHT MONITORING

CROSS-REFERENCE TO RELATED APPLICATION(S)

This application claims the benefit of priority under 35 U.S.C. § 119 to German Application No. 10 2019 126 047.7, filed Sep. 26, 2019, the contents of which is incorporated by reference herein in its entirety.

FIELD

The present disclosure relates to a blood treatment device, in particular a dialysis device, for use in (continuous) blood treatment/dialysis therapies, in particular renal replacement therapies, comprising: an extracorporeal blood circuit, a dialyzer and a dialysis fluid circuit, wherein the extracorporeal blood circuit and the dialysis fluid circuit are separated from each other via a membrane provided in the dialyzer, via which blood can be filtered (using a dialysis fluid solution); at least one bag, in particular disposable bag, which contains a fluid; at least one weighing device, in particular load cell, which is configured to measure and monitor the weight of the at least one bag; and at least one fluid pump which is configured to pump the fluid out of the bag or into the bag.

BACKGROUND

Blood treatment devices are already known from the prior art. For example, EP 0 829 265 B1 discloses a blood treatment device that comprises an interface for a disposable tubing set, a plurality of pumps such as a blood pump, a syringe pump, an effluent pump and a substitution pump, load cells for measuring the weight of bags containing fluids required for the blood treatment, a user interface comprising a display with touch screen and a control unit for controlling the processes of the blood treatment device. In particular, this document discloses that the weight of fluid in a bag is determined using load cells and is compared to a target weight of fluid calculated from the flow rate. If the actual weight and the target weight differ, the fluid supply is controlled to reduce the difference between the actual weight and the target weight. Moreover, an alarm is triggered if the weight of the fluid in the bag does not match the expected weight.

WO 1985 001 879 A1 also discloses a dialysis device with load cells for weighing the contents of a bag. In particular, the weight of the bag is to be monitored in order to detect a system failure. An alarm is generated in a case where a weight loss is not indicated although it is present and should therefore be indicated, which according to the disclosure can be the case with a kinked bag.

Further prior art can be found in EP 0 611 228 A2, U.S. Pat. No. 5,112,298 A, EP 3 034 112 A1, WO 2016 104 720 A1 and US 2011/0160649 A1.

During a blood treatment/dialysis treatment, a bag containing a fluid to be supplied to, for example, the extracorporeal blood circuit or the dialysis fluid circuit (e.g. a substitution solution) may be unintentionally pressed onto the load cell, for example when a user pulls on the bag or squeezes the bag. When the bag or load cell is pressed, a deviation/difference/fluctuation/variation usually occurs in the weight of the bag, which is measured by the load cell.

The prior art basically has the disadvantage that deviations/differences/fluctuations/variations in a weight of the bag, which are caused by unintentional pressing on the bag or on the load cell, are not adequately taken into account. In particular, the prior art does not provide for any suitable measures how to deal with this specific incident in a suitable way, in particular if it occurs during an ongoing blood treatment therapy.

SUMMARY

It is therefore the object of the present disclosure to avoid or at least reduce the disadvantages of the prior art. In particular, the blood treatment device is to be configured in such a way that deviations/differences/fluctuations/variations in a weight of the bag, which are caused by an unintentional pressing on the bag/on the load cell/of the bag on the load cell, are appropriately taken into account during an ongoing blood treatment therapy.

This object is solved in a generic blood treatment device in that it has a control unit that is configured: to cause an interruption of a fluid supply by stopping the fluid pump, if an unexpected weight variation/deviation/difference/fluctuation of the bag, caused by a malfunction, in particular unintentional pressing on the bag or the weighing device/load cell, and measured by the weighing device, is detected; to temporarily maintain the interruption of the fluid supply until the malfunction disappears, in order to avoid/prevent calculation of an incorrect fluid balance/liquid balance; to automatically restart/re-initiate the fluid supply by the fluid pump if the bag or the weight of the bag stabilizes within a predetermined time and the weight variation does not exceed a predetermined first threshold; and to generate an alarm only if the bag/the weight of the bag does not stabilize within the predetermined time and/or the weight variation/deviation/difference/fluctuation of the bag exceeds the predetermined first threshold.

The core of the disclosure is that in a case where a malfunction caused by unintentional pressing of the bag on the load cell occurs, the fluid supply is interrupted by the fluid pump being driven and stopped by the control unit. After the interruption of the fluid supply, a check is made to see if there is still a variation/deviation/difference/fluctuation in the weight of the bag. For example, if the bag is pulled or pressed only briefly and unintentionally, the weight monitored by the load cell will deviate or fluctuate only briefly and thus deviate from the actual weight of the bag and will soon settle back to the actual bag weight. The control unit maintains the interruption of the fluid supply for this time. If the weight of the bag stabilizes within a predetermined time, i.e. if the variation/difference/deviation/fluctuation in the weight of the bag disappears within the predetermined time and if at the same time the weight variation does not exceed/has not exceeded a first predetermined limit value, the fluid supply is restarted by controlling and driving the fluid pump by the control unit. However, if the weight of the bag does not stabilize within the predetermined time, i.e. if the variation/difference/deviation/fluctuation in the weight of the bag does not disappear within the predetermined time, and/or if the weight variation exceeds the predetermined first limit value, the control unit generates an alarm and the blood treatment therapy is preferably stopped.

In other words, according to the present disclosure, the alarm is raised and the blood treatment therapy is preferably stopped if the weight variation (at any time) exceeds the first predetermined limit value, which can be set to 40 grams, for example, i.e. if the weight variation is excessive. Furthermore, according to the disclosure, the alarm is raised and the blood treatment therapy is preferably stopped (which also means that the fluid supply remains interrupted) if the weight (mass) of the bag does not stabilize within the predetermined time, which can be set to, for example, one minute. It goes without saying that the alarm is also raised and the blood treatment therapy is preferably stopped if the weight variation exceeds the first predetermined limit value and the weight of the bag does not stabilize within the predetermined time. Only if both the first predetermined limit value is not exceeded and if the weight of the bag stabilizes within the predetermined time is the fluid supply automatically resumed by the fluid pump and is the blood treatment therapy continued.

The present disclosure thus provides a blood treatment device that appropriately takes into account deviations/differences/fluctuations/variations in a weight of the bag caused by unintentional pressing on the bag or load cell during an ongoing blood treatment therapy.

It is advantageous if the control unit is configured to detect an unexpected weight variation in the bag when an abrupt weight increase or decrease is detected by the load cell (an abrupt increase or decrease in an unfiltered weight value of the bag), wherein the weight increase or decrease is equal to or larger than a predetermined value. In particular, according to the present disclosure, a predetermined value could be found by tests, which in a suitable way detects malfunctions caused by unintentional pressing of the bag on the load cell. The predetermined value is preferably set between 20 and 35 grams. Tests have shown that pulling or pushing the bag usually causes a variation/deviation/difference/fluctuation of more than 35 grams. This means that the fluid supply is not interrupted in the case of smaller differences/deviations, but only when a difference/deviation is present which indicates that it is suitable for distorting the calculation of the fluid balance/liquid balance or fluid level performed by the control unit.

The control unit is advantageously configured to interrupt the fluid supply by stopping the fluid pump if the bag or the weight of the bag does not stabilize within a predetermined period of time, in particular about 10 seconds. This means that it may be provided in accordance with the disclosure that the interruption of the fluid supply (by stopping the fluid pump) is not directly/immediately effected when the weight variation of the bag is detected. According to the present disclosure, it is preferable to wait for a short time (e.g. 10 seconds). If the weight of the bag stabilizes within this short period, it is not necessary to interrupt the fluid supply. If the weight of the bag does not stabilize within this short period of time, the fluid supply is preferably stopped by the fluid pump. However, the present disclosure is not limited to this configuration example and it may also be basically provided that the interruption of the fluid supply (by stopping the fluid pump) is effected directly/immediately.

It is advantageous if the control unit generates the alarm if the bag/the weight of the bag does not stabilize within a predetermined time, in particular within one minute. It has been found that the weight of the bag will stabilize again within a relatively short period of time if the variation/difference/deviation/fluctuation in the weight of the bag is caused by unintentionally pressing the bag/on the load cell for a short time. If the variation/difference/deviation/fluctuation is present for a longer period of time, it is possible that the bag has become permanently jammed, for example, so that the blood treatment therapy has to be interrupted and the affected bag can be examined by a user.

A particularly preferred embodiment of the present disclosure is characterized in that the control unit is configured to detect an unexpected weight variation in the bag when an abrupt/sudden weight increase or weight decrease of more than 35 grams is detected by the load cell and to generate the alarm if the bag/the weight of the bag does not stabilize within one minute.

It is advantageous if the control unit is configured to detect weight variation caused by unintentional pressing on the load cell or bag.

When the unexpected weight variation of the bag is determined or detected, the control unit is advantageously configured to stop the calculation of the fluid balance immediately or directly. Thus, the variation in the weight of the bag is taken into account in a suitable manner and not erroneously included in the fluid balance. It is generally desirable that the fluid balance is calculated correctly so that the ratio between the amount of fluid withdrawn and the amount of fluid returned can be adjusted appropriately according to medical requirements.

The control unit is thus preferably configured, when the unexpected weight variation of the bag is determined or detected, to stop the calculation of the fluid balance immediately or directly, and to interrupt the fluid supply by stopping the fluid pump only if the bag or the weight of the bag does not stabilize within a predetermined period of time, in particular about 10 seconds. In other words, if an unexpected weight variation is detected, the calculation of the fluid balance is stopped immediately, while the fluid supply by the fluid pump is not stopped immediately but the system waits for a short period of time. If the weight variation stabilizes again within this short period of time, and thus stopping of the fluid supply is not necessary, the weight variation is simply calculated into the fluid balance afterwards.

It is advantageous if (in the case that the fluid supply is interrupted by stopping the fluid pump) the control unit is configured to include the weight variation in the fluid balance if the bag or the weight of the bag stabilizes within the predetermined time and the weight variation does not exceed the first predetermined limit value.

According to the disclosure, it may be provided that the weight variation is included in the fluid balance (afterwards), in particular if the fluid supply by the fluid pump is continued, i.e. is not interrupted at all, or if the fluid supply by the fluid pump is resumed after an interruption.

If the weight variation does not exceed the first predetermined limit value, i.e. is less than or equal to the first predetermined limit value, and if the bag or the weight of the bag stabilizes within the predetermined time, the control unit is configured to automatically restart or re-initiate the fluid supply by the fluid pump, not to raise an alarm, and to include the weight variation in the fluid balance.

Furthermore, if the weight variation exceeds the predetermined first limit value and does not exceed a predetermined second limit value, i.e. lies between the first predetermined limit value and the second predetermined limit value, and the bag or the weight of the bag stabilizes within the predetermined time, the control unit is preferably configured to generate the alarm and to ask a user via a user interface whether or not the weight variation should be included in the fluid balance. In this special case, in which the weight of the bag basically stabilizes again, and the weight variation was not too large (smaller than the predetermined second limit value), the user can thus decide in an advantageous way afterwards by an appropriate input whether he wants to include the weight variation in the fluid balance. In practice, this is regularly accompanied by a resumption of the blood treatment therapy by the user.

Alternatively, however, the user can decide not to include the weight variation in the fluid balance. In practice, this is regularly accompanied by a termination of the blood treatment therapy.

If the weight variation exceeds the predetermined first limit value and does not exceed a/the predetermined second limit value, i.e. lies between the first predetermined limit value and the second predetermined limit value, and the bag or the weight of the bag does not stabilize within the predetermined time, the control unit is preferably configured to generate the alarm, to keep the fluid supply interrupted, and not to include the weight variation in the fluid balance.

If the (unexpected, unfiltered) weight variation of the bag exceeds a/the second predetermined limit value, i.e. is greater than the second predetermined limit value, the control unit is preferably configured to generate an immediate alarm, to interrupt or keep the fluid supply interrupted, and not to include the weight variation in the fluid balance.

If the (unfiltered) weight of the bag stabilizes within the predetermined time, but the (unexpected, unfiltered) weight variation of the bag exceeds a/the second predetermined limit value, the control unit can advantageously also be configured to generate the alarm and not to include the weight variation in the fluid balance.

Preferably, the predetermined time (preferably one minute) is greater than the aforementioned predetermined time period (about 10 seconds). In particular, the predetermined time is one minute or 60 seconds and the predetermined time period is 10 seconds.

Preferably, the predetermined second limit value is greater than the predetermined first limit value, and the predetermined first limit value is greater than the predetermined value (between 20 and 35 grams, in particular 35 grams). The predetermined first limit value is preferably 40 grams. Further preferably, the predetermined second limit value is preferably 80 grams.

The extracorporeal blood circuit and the dialysis fluid circuit are preferably designed as disposable tubes, which are attached to an interface provided on the dialysis device.

Furthermore, it is practical if the blood treatment device is equipped with a bar code reader, which is configured to read bar codes on disposable items such as disposable tubing or their packaging.

Moreover, it is practical if the blood treatment device has a user interface comprising a display with touch screen.

The blood treatment device is preferably configured for wired communication.

The control unit of the blood treatment device is preferably designed as at least one processor, preferably several processors.

In other words, the disclosure relates to a dialysis device. The dialysis device includes a bar code reader. Furthermore, the dialysis device contains a user interface or a display with a touch screen. The dialysis device also has an interface for a disposable tubing set containing a blood side and a dialysis-fluid side separated by a (semi)permeable membrane for filtering blood using a dialysis fluid solution/dialysis solution. A substitution solution/replacement solution is supplied to the blood side before/after a dialyzer. The dialysis device has a blood pump, a syringe pump, an effluent pump, a substitution solution pump etc. The dialysis device is configured for wired communication/has wired or wire-connected communication facilities. The dialysis device is characterized by a software that is particularly suitable for use in continuous dialysis therapies, such as renal replacement therapy. The software runs on a large number of processors within the dialysis device. The dialysis device also has an energy management device (integrated circuit). The dialysis device also contains weighing devices, in particular load cells, which measure the weight of disposable bags containing the fluids (e.g. dialysis fluid solution, substitution solution) required for the dialysis therapy.

The present disclosure provides in particular improved bag weight monitoring. If bags are unintentionally pressed on the load cell or another (similar) unexpected fluctuation is detected, the blood treatment device (a control unit thereof) automatically stops the fluid pump/fluid pumps and interrupts the therapy. In order to prevent the machine/dialysis device/blood treatment device (the control unit) from calculating an incorrect fluid balance/an incorrect fluid equilibrium, this interruption is maintained until the malfunction disappears. If the bag does not stabilize within one minute/If the bag is not stabilized within one minute, an alarm is generated. According to a preferred configuration example, an alarm is generated when an unstable weight greater than 35 grams is present and the fluctuation in the weight lasts longer than one minute.

BRIEF DESCRIPTION OF THE DRAWING FIGURES

The disclosure is further explained in the following with the help of figures. These show.

DETAILED DESCRIPTION

The figures are merely schematic in nature and serve exclusively for understanding the present disclosure. The same elements are marked with the same reference signs.

Figure 1:
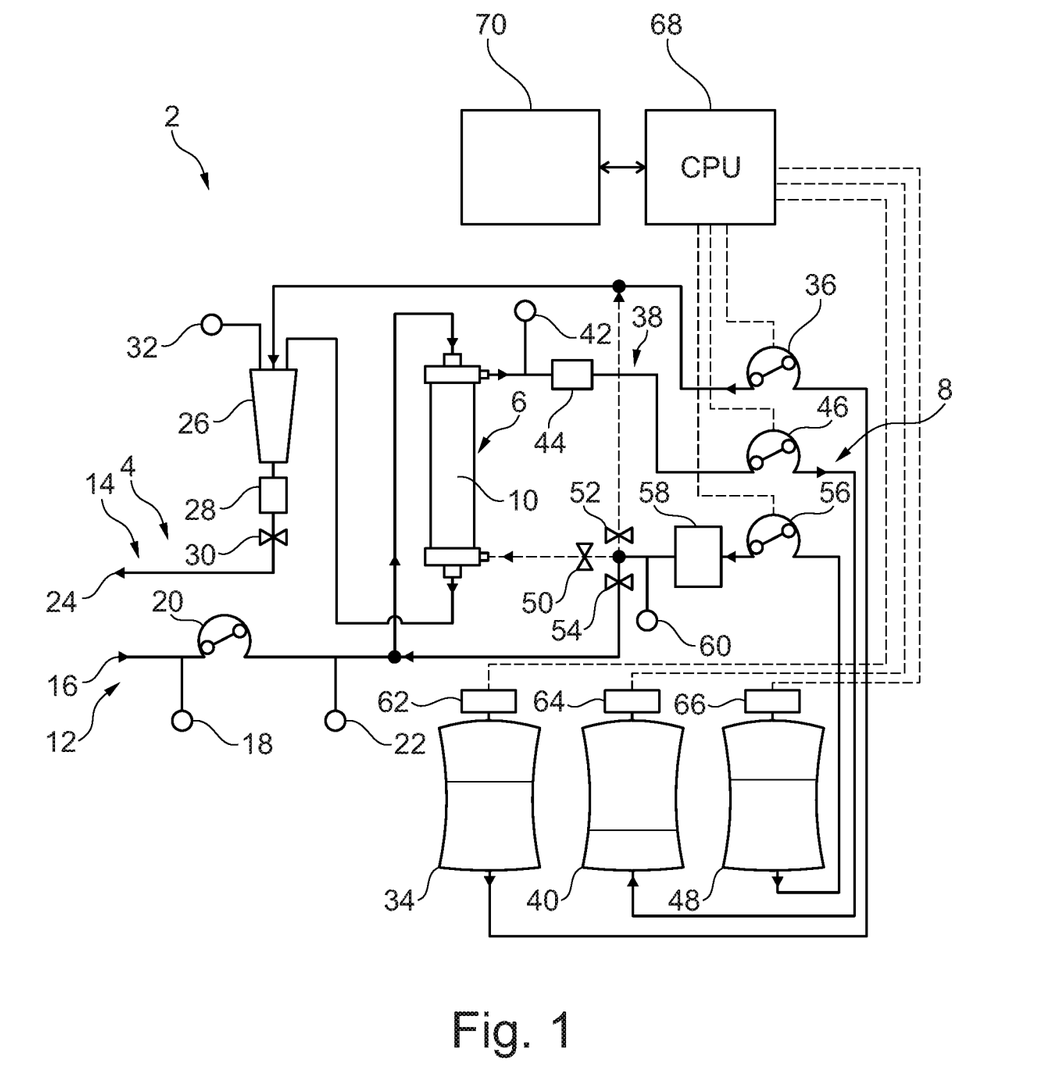
FIG. 1 shows a schematic view of a blood treatment device according to the present disclosure.

FIG. 1 shows a schematic view of an extracorporeal blood treatment device (dialysis device) 2. The blood treatment device 2 is basically configured to be used in both continuous and intermittent blood treatment therapies, in particular renal replacement therapies. The blood treatment device 2 is configured in particular as an acute dialysis machine or an acute dialysis device and is thus essentially prepared for use in intensive care units with predominantly unstable patients. With the blood treatment device 2 of the present disclosure, principally a variety of different blood treatment therapies can be performed (e.g. slow continuous ultrafiltration (SCUF), continuous veno-venous hemofiltration (CVVH), continuous veno-venous hemodialysis (CVVHD), continuous veno-venous hemodiafiltration (CVVHDF), therapeutic plasma exchange (TPE), etc.) as well as dilution modes (e.g., pre-dilution, post-dilution, pre-dilution and post-dilution) and anticoagulation types (e.g., none, heparin, citrate, etc.).

The blood treatment device 2 basically has an extracorporeal circuit 4, a dialyzer (hemofilter) 6 and a dialysis fluid circuit 8. The extracorporeal circuit 4 and the dialysis fluid circuit 8 are separated by a membrane 10 provided in the dialyzer 6, through which blood can be filtered using a dialysis fluid solution or without using a dialysis fluid solution.

The extracorporeal circuit 4 comprises an arterial portion 12 and a venous portion 14. In principle, it is provided that the arterial portion 12, in particular one end thereof, is to be connected or attached to an artery of a patient, in particular an intensive care patient. It is also provided that the venous portion 14, in particular one end thereof, is to be connected or attached to a vein of a patient, in particular an intensive care patient.

The arterial portion 12 has, starting from an arterial end 16 in a blood flow direction towards the dialyzer 6, an arterial pressure sensor 18, an (arterial) blood pump 20, and a dialyzer inlet pressure sensor 22. Starting from the dialyzer 6 in a blood flow direction towards a venous end 24, the venous portion 14 has a venous expansion chamber or air trap 26, a safety air detector 28 and a safety valve 30. A venous pressure can be measured on/behind the venous expansion chamber 26 using a venous pressure sensor 32.

As shown in FIG. 1, the venous expansion chamber 26 is connected to a substitution solution bag/container 34. A substitution solution pump 36 is provided and configured to pump a substitution solution from the substitution solution bag 34 into the extracorporeal blood circuit 4, in particular into the venous portion 14 thereof (into the venous expansion chamber 26).

The dialysis fluid circuit 8 has at least one outlet 38 for effluent/used dialysis fluid (dialysate)/another fluid. In principle, the effluent/dialysate/the other liquid can flow through the outlet 38 from the dialyzer 6 to a collecting bag/container 40 for effluent/dialysate/etc. In the outlet 38, an effluent pressure sensor 42, a blood leak detector 44 and an effluent pump 46 are arranged or provided in a direction of flow from the dialyzer 6 to the collecting bag 40.

As can be further seen in FIG. 1, a further bag/container 48 is provided in addition to the substitution solution bag 34 and the collecting bag 40. Depending on the desired blood treatment therapy to be performed, the bag 48 may contain, for example, a substitution solution/fluid or a dialysis fluid.

When, for example, a hemodialysis/hemodiafiltration treatment etc. is to be carried out with the extracorporeal blood treatment device 2, i.e. a blood treatment therapy in which dialysis fluid flows through the dialyzer 6 and thus a substance transport from the extracorporeal circuit 4 to the dialysis fluid circuit 8 takes place both by diffusion and convection, then the bag 48 contains dialysis fluid. When a first valve 50 is now opened and both a second valve 52 and a third valve 54 are closed, then the dialysis fluid can be pumped to the dialyzer 6 via a pump 56.

When, for example, hemofiltration etc. is to be performed with the extracorporeal blood treatment device 2, i.e. a blood treatment therapy in which no dialysis fluid flows through the dialyzer 6 and thus substance transport from the extracorporeal circuit 4 to the dialysis fluid circuit 8 takes place only via convection/filtration, the bag 48 can contain a substitution solution. When the first valve 50 and the second valve 52 are closed and the third valve 54 is opened, the substitution solution can be pumped from the bag 48 into the arterial portion 12 of the extracorporeal circuit 4 (pre-dilution). When the first valve 50 and the third valve 54 are closed and the second valve 52 is opened, the substitution solution can be pumped from the bag 48 into the venous portion 14 of the extracorporeal circuit 4 (post-dilution). When the first valve 50 is closed and the second valve 52 and the third valve 54 are opened, the substitution solution can be pumped from the bag 48 into both the arterial portion 12 and the venous portion 14 of the extracorporeal circuit (pre-dilution and post-dilution). According to the present disclosure, pre-dilution and post-dilution can also be achieved by pumping the substitution solution from the substitution solution bag 34 via the substitution solution pump 36 into the venous portion 14 of the extracorporeal circuit 4 (post-dilution) and simultaneously pumping the substitution solution from the bag 48 via the pump (substitution solution pump) 56 into the arterial portion 12 of the extracorporeal circuit 4 (pre-dilution).

As shown in FIG. 1, a fluid warmer 58 and a pressure sensor 60 are provided between the pump 56 and the valve assembly consisting of the first valve 50, the second valve 52, and the third valve 54.

The three bags, i.e. the substitution solution bag 34, the collecting bag 40 and the bag 48, each have load cells attached to them, namely a first load cell 62, a second load cell 64 and a third load cell 66. The first load cell 62 is basically configured to measure or monitor the weight of the substitution solution bag 34. The second load cell 64 is basically configured to measure or monitor the weight of the collecting bag 40. The third load cell 66 is basically configured to measure or monitor the weight of the bag 48. The load cells 62, 64, 66 are basically examples of weighing devices. The present disclosure is not limited to the fact that the weighing devices are designed as load cells 62, 64, 66. Basically, any other weighing device/scale/force transducer can also be provided, as long as it enables the weight/mass of a bag to be measured or monitored.

The extracorporeal blood treatment device 2 furthermore has a control unit (CPU) 68, which receives information from the sensors provided in the blood treatment device 2 and which controls the actuators provided in the blood treatment device 2. According to the disclosure, this provides software-supported therapy in particular. The control unit 68 receives in particular information from the arterial pressure sensor 18, the dialyzer inlet pressure sensor 22, the safety air detector 28, the venous pressure sensor 32, the effluent pressure sensor 42, the blood leak detector 44, the pressure sensor 60, the first load cell 62, the second load cell 64, the third load cell 66, etc. The control unit 68 controls in particular the blood pump 20, the safety valve 30, the substitution solution pump 36, the effluent pump 46, the first valve 50, the second valve 52, the third valve 54, the pump 56, the fluid warmer 58, etc. Furthermore, the control unit 68 exchanges information with a user interface 70 designed as a display with touch screen. For example, the control unit 68 may be configured to display a warning or an alarm on the user interface 70. Furthermore, information entered by a user/operator on the user interface 70 can be transferred to the control unit 68.

As already shown in FIG. 1, the present disclosure essentially relates to the controlling of the substitution solution pump 36, the effluent pump 46, and the pump 56 on the basis of the information obtained from the first load cell 62, the second load cell 64, and the third load cell 66. The present disclosure essentially relates to the control by the control unit 68. When the control unit 68 detects/measures the occurrence of an unexpected weight variation of the substitution solution bag 34 based on information provided by the first load cell 62, the control unit 68 controls the substitution solution pump 36 to stop it in order to effect an interruption of the fluid supply. When the control unit 68 detects/measures the occurrence of an unexpected weight variation of the collecting bag 40 based on information provided by the second load cell 64, the control unit 68 controls the effluent pump 46 to stop it in order to effect an interruption of the fluid supply. When the control unit 68 detects/measures the occurrence of an unexpected weight variation of the bag 48 based on information provided by the third load cell 66, the control unit 68 controls the pump 56 to stop it in order to effect an interruption of the fluid supply.

Therefore, it generally applies that when the term 'bag' is used in accordance with the present disclosure, the substitution solution bag 34, the collecting bag 40 as well as the bag 48 may be meant. Furthermore, when the present disclosure generally refers to a weighing device or a load cell, the first load cell 62, the second load cell 64 as well as the third load cell 66 may be meant. In addition, when the present disclosure generally refers to a fluid pump, the substitution solution pump 36, the effluent pump 46 as well as the pump 56 may be meant.

Figure 2:
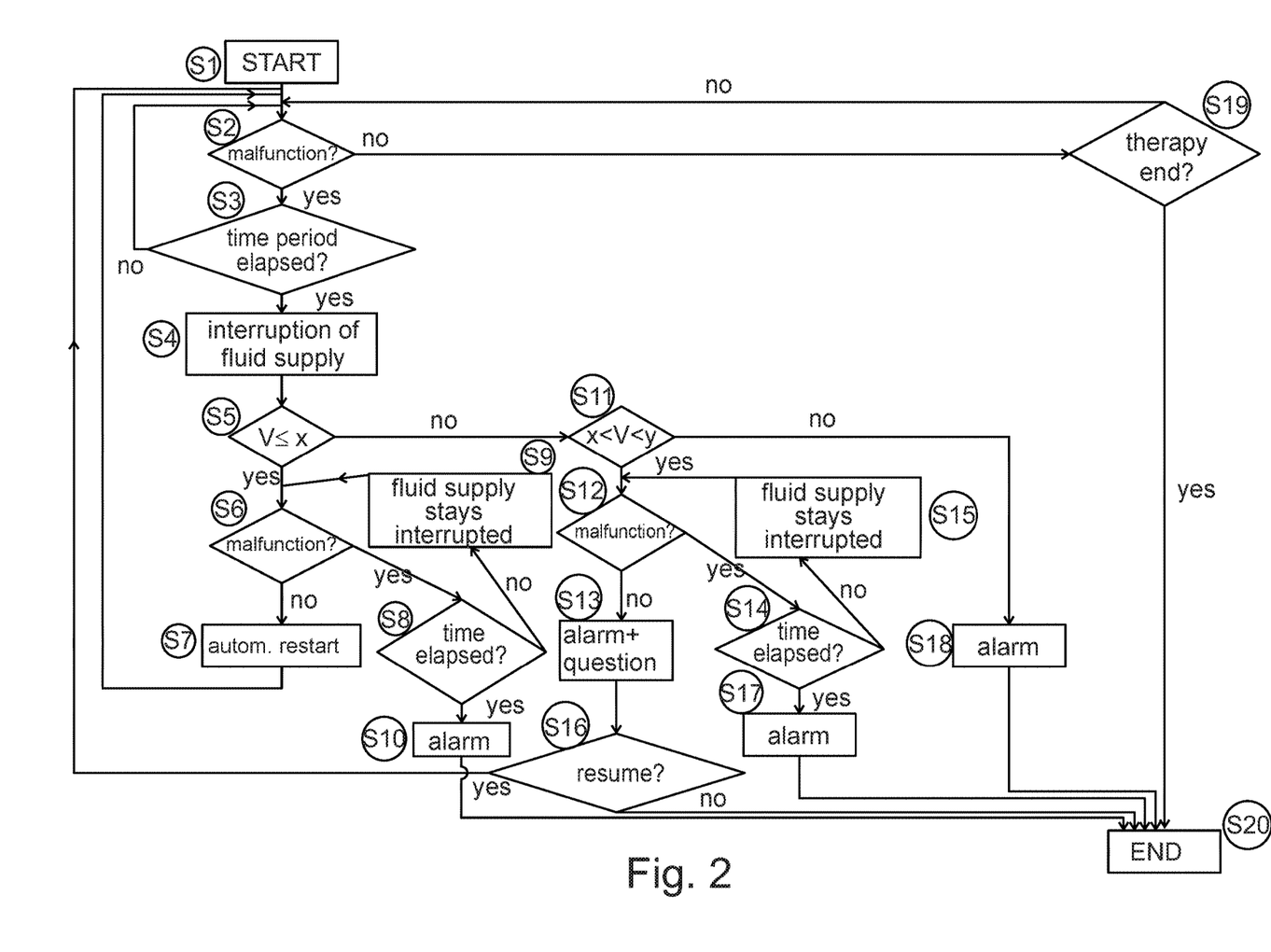
FIG. 2 shows a flow chart illustrating the improved bag weight monitoring running in the control unit according to the disclosure.

FIG. 2 shows the course of the improved bag weight monitoring in accordance with the disclosure. The control unit 68 of the present disclosure basically receives information from a load cell (for example the first load cell 62, the second load cell 64, and the third load cell 66), which continuously measures and monitors the weight of a bag (for example of the substitution solution bag 34, the collecting bag 40, and the bag 48) containing a liquid/fluid. From this information, the control unit 68 can determine at 'S2' whether there is an unexpected weight variation/difference/fluctuation/deviation in the weight of the bags 34, 40 or 48 caused by a malfunction.

An unexpected weight variation caused by a malfunction is usually detected by the control unit 68 when an abrupt weight increase or weight reduction is detected by a load cell 62, 64 or 66 which is greater than or equal to a predetermined value (e.g. 20 grams).

If a malfunction is detected ('yes'), the control unit 68 checks at 'S3' whether a predetermined time period (e.g. 10 seconds) has already passed since the malfunction first occurred. If the bag 34, 40, 48 or the weight of the bag 34, 40, 48 does not stabilize within the predetermined time period, i.e. if the malfunction continues to exist beyond the predetermined time period, the fluid supply is interrupted by stopping the fluid pump 36, 46 or 56 at 'S4'. This means, for example, that no more liquid is pumped out of the substitution solution bag 34 by the substitution solution pump 36, that, for example, no more liquid is pumped by the effluent pump 46 into the collecting bag 40, and that, for example, no more liquid is pumped out of the bag 48 by the pump 56.

However, if the weight of the bag 34, 40 or 48 has already stabilized within the aforementioned predetermined time period (in particular within 10 seconds) (i.e. there is no longer a malfunction, cf. at 'S2'), there is preferably no interruption of the fluid supply by the fluid pump 36, 46 or 56.

When the fluid supply is interrupted, a check is made at 'S5' whether the weight variation 'V' does not exceed a predetermined first limit value x. For example, the predetermined first limit value x can be set to 40 grams. If the predetermined first limit value x is not exceeded ('yes'), the control unit 68 checks at 'S6' whether the malfunction has disappeared or is still present. As long as the malfunction is present, the interruption of the fluid supply is maintained (see at 'S9'). If the bag 34, 40 or 48 or the weight of the bag 34, 40 or 48 stabilizes within a predetermined time (e.g. one minute), i.e. there is no longer a malfunction, the fluid supply is automatically restarted/re-initiated by the fluid pump 36, 46 or 56 at 'S7'. If the bag 34, 40 or 48 does not stabilize within the predetermined time, an alarm is raised at 'S10'.

If at 'S5' the control unit 68 determines ('no') that the weight variation 'V' exceeds the first predetermined limit value x, at 'S11' the control unit 68 checks whether the weight variation 'V' lies between the first predetermined limit value x and a second predetermined limit value y. The second predetermined limit value y can be set to 80 grams, for example. If 'V' lies within this range ('yes'), the control unit 68 checks at 'S12' whether the malfunction has disappeared or is still present. As long as the malfunction is present, the interruption of the fluid supply is maintained (see at 'S15'). If the bag 34, 40 or 48 or the weight of the bag 34, 40 or 48 stabilizes within a predetermined time (e.g. one minute), i.e. there is no longer a malfunction, an alarm is generated at 'S13' and a user is asked via the user interface 70 whether he wants to calculate the weight variation in the fluid balance or not. As an option, it may be provided according to the present disclosure that the user can decide to resume the blood treatment therapy afterwards (at 'S16'). If the bag 34, 40 or 48 does not stabilize within the predetermined time, an alarm is raised at 'S17'.

If at 'S11' the control unit 68 determines that the weight variation 'V' is above the second predetermined limit value y ('no' at 'S11'), an alarm is raised at 'S18'.

The present routine ends when the alarm is raised, or when the end of therapy is reached, or when the user decides at 'S16' not to resume the blood treatment therapy.

Figure 3:
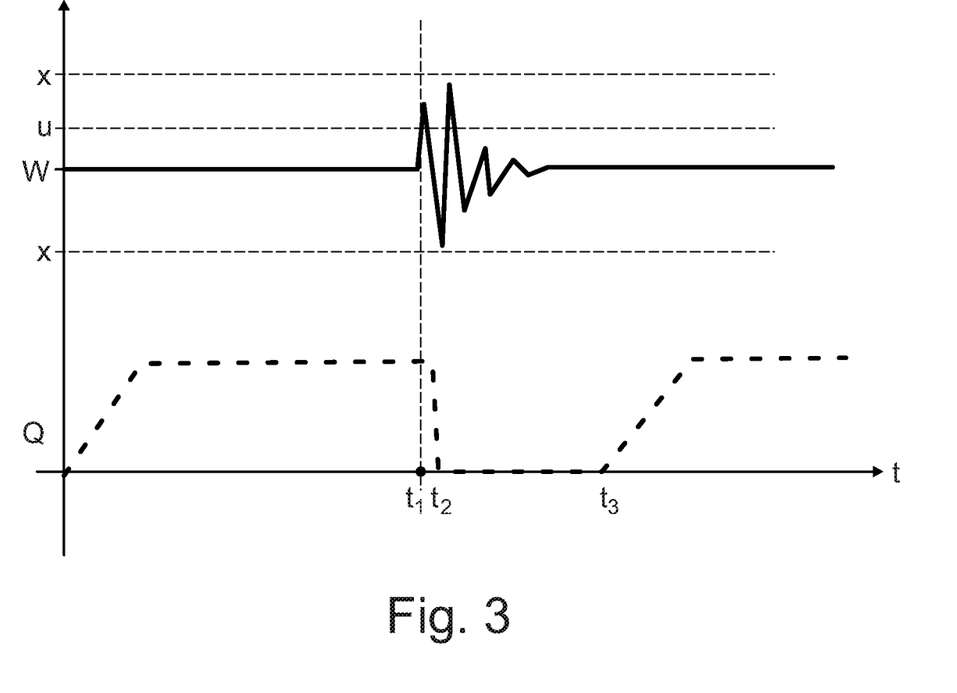
FIG. 3 shows a diagram showing a time course of a weight of a bag and a flow rate of a fluid pump, which pumps a fluid out of or into the bag, according to the present disclosure.

FIG. 3 shows a diagram illustrating a time course of a bag weight 'W' and a fluid pump flow rate 'Q', which pumps a fluid out of the bag 34, 48 or into the bag 40, according to the present disclosure. At time t1, FIG. 3 shows that a weight variation of the bag weight 'W' is greater than a predetermined value u (for example 20 grams). At time t1, the control unit 68 thus detects an unexpected weight variation in a bag 34, 40, 48, since an abrupt weight increase (greater than the predetermined value u) was detected by a load cell 62, 64, 66.

As shown in FIG. 3, the flow rate Q of a fluid pump 36, 46, 56 is not immediately interrupted at time t1, but the control unit waits for a predetermined short time period, for example about 10 seconds. In the present case, the bag weight 'W' does not stabilize within the predetermined short time period. This is because the control unit 68 determines at time t2 that the bag weight 'W' has not stabilized within the time period. Against this background, the control unit 68 stops the fluid pump 36, 46, 56 at time t2 and thus interrupts the fluid supply. Accordingly, the fluid pump flow rate 'Q' is reduced to zero at time t2.

The control unit 68 subsequently determines that the predetermined first limit value x (for example 40 grams) of the weight variation is not exceeded. Furthermore, the control unit 68 determines that the weight of the bag 34, 40, 48 has stabilized again within the predetermined time (for example one minute) to t3.

Since both conditions of the present disclosure are fulfilled, i.e. since the weight variation does not exceed the first predetermined limit value x and the bag weight 'W' stabilizes within the predetermined time, the fluid supply is automatically restarted/re-initiated by the fluid pump 36, 46, 56.

What is claimed:

1. A blood treatment device for use in blood treatment therapies, the blood treatment device comprising:
    an extracorporeal blood circuit, a dialyzer and a dialysis fluid circuit, wherein the extracorporeal blood circuit and the dialysis fluid circuit are separated from each other via a membrane provided in the dialyzer, via which blood can be filtered;
    a bag having a weight, which contains a fluid;
    a weighing device configured to measure and monitor the weight of the bag;
    a fluid pump configured to pump the fluid out of the bag or into the bag; and a control unit, which is configured:
- to effect an interruption of a fluid supply by stopping the fluid pump when a weight variation of the bag caused by a malfunction and measured by the weighing device occurs;
- to temporarily maintain the interruption of the fluid supply, at least until the malfunction disappears;
- to automatically restart or re-initiate the fluid supply by the fluid pump if the bag or the weight of the bag stabilizes within a predetermined time and the weight variation does not exceed a first predetermined limit value; and
- to generate an alarm only if the bag or the weight of the bag does not stabilize within the predetermined time and/or if the weight variation exceeds the first predetermined limit value.

2. The blood treatment device according to claim 1, wherein the control unit is configured to detect the weight variation in the bag when a weight increase or weight decrease is detected by the weighing device, wherein the weight increase or weight decrease is equal to or greater than a predetermined value.

3. The blood treatment device according to claim 2, wherein the predetermined value is between 20 grams and 35 grams.

4. The blood treatment device according to claim 1, wherein the control unit is configured to interrupt the fluid supply by stopping the fluid pump if the bag or the weight of the bag does not stabilize within a predetermined time period.

5. The blood treatment device according to claim 1, wherein the control unit is configured to stop the calculation of the fluid balance immediately or directly if the weight variation in the bag is determined or detected.

6. The blood treatment device according to claim 1, wherein the control unit is configured to include the weight variation in the bag in the fluid balance if the bag or the weight of the bag stabilizes within the predetermined time and the weight variation does not exceed the first predetermined limit value.

7. The blood treatment device according to claim 1, wherein the control unit is configured to automatically restart or re-initiate the fluid supply by the fluid pump and to calculate the weight variation in the bag into the fluid balance if the weight variation in the bag is less than or equal to the first predetermined limit value, and the bag or the weight of the bag stabilizes within the predetermined time.

8. The blood treatment device according to claim 1, wherein the control unit is configured to generate the alarm and to ask a user via a user interface whether or not to include the weight variation in the bag in the fluid balance when the weight variation exceeds the first predetermined limit value and is less than a second predetermined limit value, and the bag or the weight of the bag stabilizes within the predetermined time.

9. The blood treatment device according to claim 1, wherein the control unit is configured to generate the alarm, to keep the fluid supply interrupted and not to include the weight variation in the bag in the fluid balance if the weight variation exceeds the first predetermined limit value and is less than a second predetermined limit value, and the bag or the weight of the bag does not stabilize within the predetermined time.

10. The blood treatment device according to claim 1, wherein the control unit is configured to generate the alarm, to keep the fluid supply interrupted and not to include the weight variation in the bag in the fluid balance if the weight variation in the bag exceeds a second predetermined limit value.

* * * * *